United States Patent [19]

Liotta et al.

[11] Patent Number: 5,270,447
[45] Date of Patent: Dec. 14, 1993

[54] METALLOPROTEINASE PEPTIDES: ROLE IN DIAGNOSIS AND THERAPY

[75] Inventors: Lance A. Liotta, Potomac; William Stetler-Stevenson, Gaithersburg; Henry Krutzsch, Bethesda, all of Md.

[73] Assignee: The United States of America as represented by the Department of Health & Human Services, Washington, D.C.

[21] Appl. No.: 317,407

[22] Filed: Mar. 1, 1989

Related U.S. Application Data

[63] Continuation-in-part of Ser. No. 196,242, May 20, 1988, and a continuation-in-part of Ser. No. 248,420, Sep. 23, 1988.

[51] Int. Cl.$^5$ .................... A61K 37/02; C12N 11/08
[52] U.S. Cl. .................... 530/326; 530/330; 435/184
[58] Field of Search .......... 435/7, 91, 222, 184; 514/8; 530/326, 330

[56] References Cited

PUBLICATIONS

McKerrow, *The Journal of Biological Chemistry*, vol. 262, No. 13, May 5, 1987, p. 5943.
Fini, et al. *Biochemistry* 1987, 26, 6156-6165.
Article entitled "Molecular Cloning" A Laboratory Manual by T. Maniatis; E. F. Fritsch; J. Sambrook; Chapter 12 Vectors that Express Cloned DNA in *Escherichia coli*.

*Primary Examiner*—Margaret Moskowitz
*Assistant Examiner*—Bradley L. Sisson
*Attorney, Agent, or Firm*—Robert Benson

[57] ABSTRACT

A family of metalloproteinases exist which cleave extracellular matrix molecules. These metalloproteinases are secreted in a latent inactive form and require activation in order to specifically cleave the preferred substrate. A series of peptides have been prepared based on the complete sequence analysis of type IV Procollagenase. Peptide inhibitors were synthesized which correspond to cysteine repeat regions and histidine containing regions; the mechanism of action of these peptides involves inhibition of binding of the enzyme to the substrate. Peptide inhibitors were synthesized which correspond to the peptide cleaved off during activation, and constitute a novel class of metalloproteinase inhibitors. These inhibitors are members of a series of peptides which contain the core amino acid sequence PRCG. The cysteine residue is required for activity. Affinity purified antibodies directed against specific peptides can be used to a) detect any general metalloproteinase enzyme with the sequence in part VAAHE or PRCGNPD, and distinguish it from other known members of the metalloproteinase family, b) block functional domains resulting in the inhibition of enzyme activity, and c) distinguish latent from activated forms of the enzyme.

3 Claims, 13 Drawing Sheets

TYPE IV PROCOLLAGENASE AMINO ACID SEQUENCE

Figure 3D:
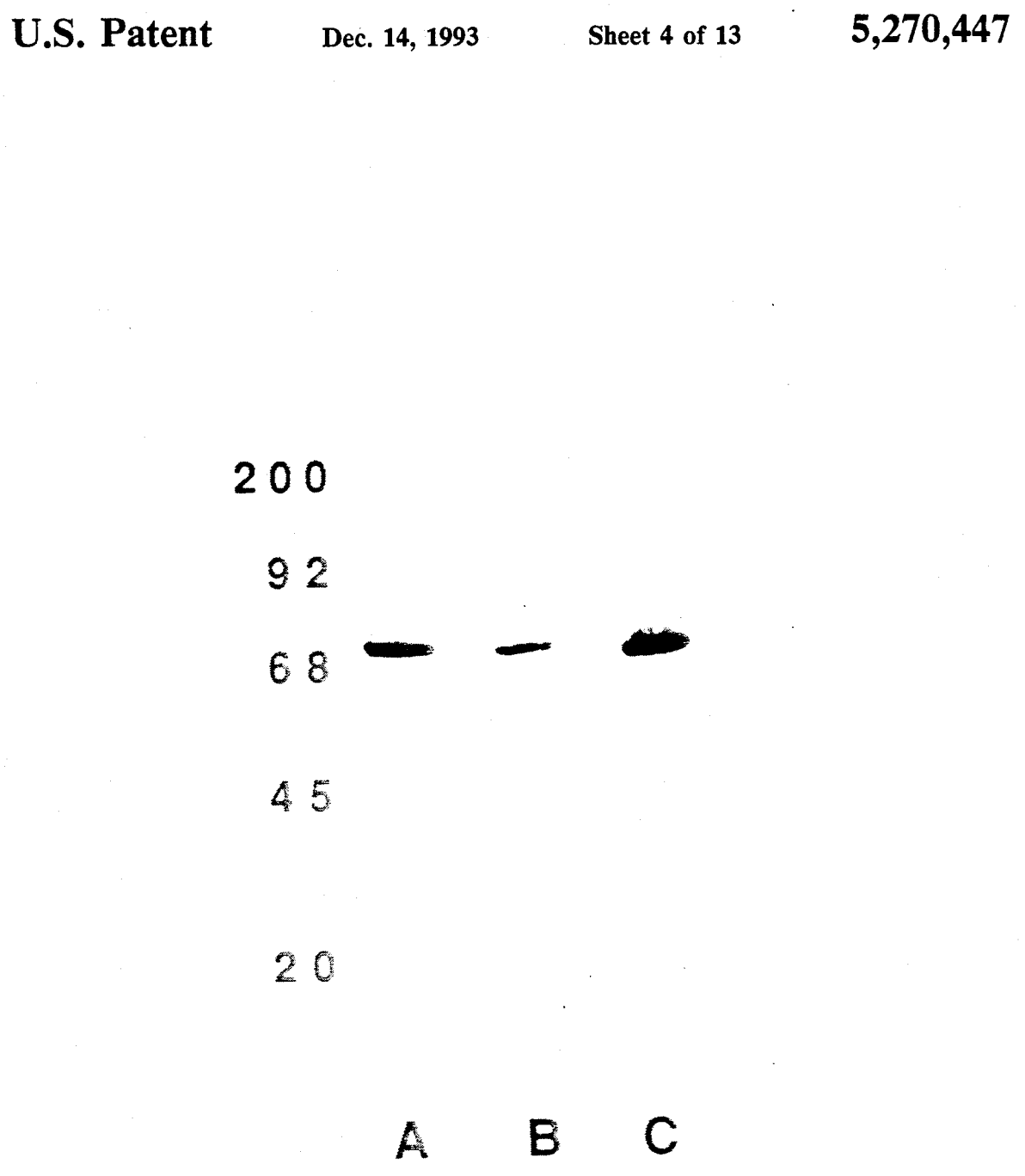

GELATIN ZYMOGRAM
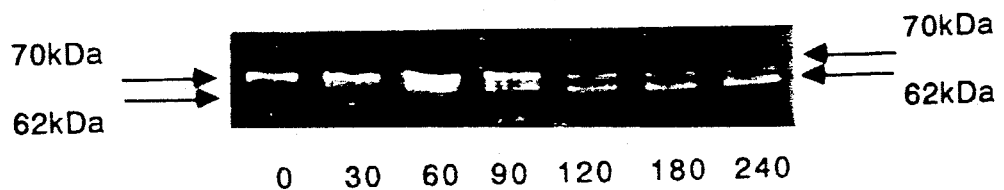
Antibody A472-490
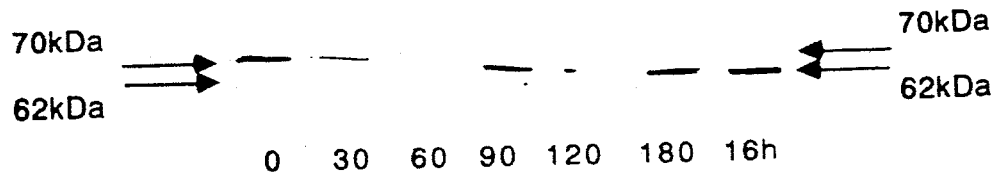
Antibody A1-17
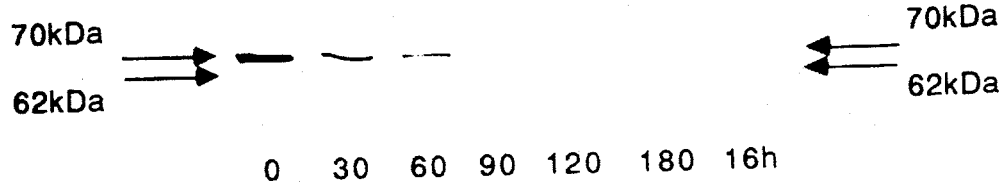
FIG. 7.

LATENT: A P S P I I K F P G D V A P

ACTIVATED: Y N F F P R K P K W D K N Q

CLEAVAGE SITE: P D V A N Y N F F P R K
　　　　　　　　　　　 8 0 8 1

MWM　　A　　B

```
          10         20         30         40         50
APSPIIKFPGDVAPKTDKELAVQ-YLNTFYGCPKESCNLFVL-KDT-----LKK----MQK

FPATLETQEQDVDLVQKYLEKYYNLKNDGRQVEKR-RNSGPVVEKLK----QMQE

YPLDGAARGEDTSMNLVQKYLENYYDLEKDVKQ-FVRRKDSGPVV---KKIREMQK 60         70         80         90        100        110
FFGLPQTGDLDQNTIETMRKPRCGNPDVANYNFFPRKPKWDKNQITYRIIGYTPDLDPET
                              * * *
FFGLKVTGKPDAETLKVMKQPRCGVPDVAQFVLTEGNPRWEQTHLRYRIENYTPDLPRAD
                              *
FLGLEVTGKLDSDTLEVMRKPRCGVPDVGHFRTFPGIPKWRKTHLTYRIVNYTPDLPKDA

```
  1           10              20              30              40              50
APSPIIKFPGDVAPKTDKELAVQ-YLNTFYGCPKESCNLFVL-KDT-----LKK---MQK

APSPIIKFPGDVAPKTDK  NOT ACTIVE

ELAVQYLNTFYGCPK  NOT ACTIVE 60              70              80              90             100             110
FFGLPQTGDLDQNTIETMRKPRCGNPDVANYNFFPRKPKWDKNQITYRIIGYTPDLDPET

TMRKPRCGNPDVANYNFFPRKPKWDKNQ  NOT ACTIVE

TMRKPRCGNPDVANYNFFPRKPK  ACTIVE

TMRKPRCGNPDVAN  ACTIVE
```

FIG. 12

METALLOPROTEINASE PEPTIDES: ROLE IN DIAGNOSIS AND THERAPY

This application is a continuation-in-part of application 07/196,242, filed May 20, 1988, and of application 07/248,420, filed Sep. 23, 1988, both pending.

BACKGROUND OF THE INVENTION

1. Field of the invention

This invention relates to peptides useful in metalloproteinase detection and inhibition. Specifically, the invention relates to peptides derived from the sequence of type IV collagenase which correspond to domain of the enzyme involved in enzyme activation and interaction of the enzyme with the substrate. Antibodies recognizing the peptides are useful in enzyme detection. Specific peptides, identified based on functional studies, constitute new classes of metalloproteinase inhibitors.

2. Background

The degradation of interstitial and basement membrane collagens is initiated by a specific class of metalloproteinases, the collagenases (EC 3.4.24.7), which are secreted into the extracellular matrix in zymogen form. The interstitial collagenases which degrade collagen types I, II and III have been characterized with respect to substrate specificity and requirements for activation (1-5).

Pepsinized type IV collagen is not susceptible to degradation by these enzymes, but is instead degraded in a specific fashion by an enzyme that has been identified in human tumor cells (6,7,11,14,17), endothelial cells (8), bone (24), fibroblasts (17), polymorphonuclear leukocytes (9) and macrophages (10). This enzyme, referred to as type IV collagenase (11,17) is a neutral metalloproteinase of 68 to 72 kilodaltons which is secreted in zymogen form (11-13). This enzyme has been closely linked to the metastatic potential of tumors in murine tumor models (14) and is augmented following the H-ras oncogene induced genetic induction of the metastatic phenotype (15,16). Trypsin treatment results in activation of the latent enzyme and a concomitant reduction in the molecular mass (12). Organomercurial compounds have also been shown to activate this enzyme, and these are also associated with a reduction in the molecular mass (17,24). The activated enzyme cleaves type IV collagen to generate characteristic ¼ amino-terminal and ¾ carboxy-terminal fragments (12,17,18). It has also been demonstrated that gelatinolytic activity is associated with this enzyme (17,19,24) as well as a type V collagenolytic activity (17,24).

Type IV collagenase has been purified from human melanoma cells and sequence information on the intact protein amino terminus has been obtained as well as on tryptic and cyanogen bromide peptide fragments (19). The sequence information demonstrates that type IV collagenase shows limited sequence homology to interstitial collagenase and stromelysin. A recent report has characterized a partial cDNA clone for a metalloproteinase secreted by H-ras-transformed human bronchial epithelial cells (17). The transformed bronchial epithelial enzyme is capable of specifically degrading type IV collagen, and the deduced amino acid sequence shows identity with that reported for tryptic and cyanogen bromide fragments of human tumor type IV collagenase (19). Thus, human melanoma cell type IV collagenase appears identical with the enzyme from H-ras-transformed bronchial epithelial cells, which is also found in fibroblasts (17) and bone cell explants (24).

SUMMARY OF THE INVENTION

The complete amino acid sequence has now been analyzed and a series of inhibitory synthetic peptides corresponding to a variety of domains of the peptide have been prepared. These peptide sequences were found in the 80 residue amino terminus, a cysteine-rich interior domain, a histidine-containing region and in a region 159 residues from the carboxy terminus. These peptides have been used to generate antibodies against specific domains within the type IV collagenase molecule. In the present invention, the antibodies, direct amino acid sequence analysis, and peptides have been used to determine a) the region of the enzyme involved in binding and interaction with the substrate, and b) the structure of the major type IV collagenase conversion product produced during zymogen activation with the organomercurial compound p-aminophenylmercuric acetate.

The discoveries stemming from this analysis have led to identification of a) a region near the amino terminus of type IV collagenase which constitutes an intrinsic enzyme inhibitor which may block the active site of the enzyme when the enzyme is in a latent state, and b) a region near the middle of the enzyme involved in binding and interaction with the substrate. Peptides homologous to these regions constitute novel metalloproteinase inhibitors.

DESCRIPTION OF THE DRAWINGS

FIG. 1 illustrates the complete amino acid sequence of human type IV procollagenase secreted by tumor cells.

FIGS. 3A, 3B, 3C, and 3D (FIG. 3A) ELISA characterization of antipeptide antibody A1-17. The synthetic peptide corresponding to the amino terminal residues 1 through 17 of type IV procollagenase was synthesized and used an an antigen. The peptide-bovine serum albumin conjugate was used as coating antigen in this ELISA.

FIG. 3B ELISA characterization of antipeptide antibody A472-490. The synthetic peptide corresponding to the internal residues 472-490 of type IV procollagenase was synthesized and used as an antigen. The peptide-bovine serum albumin conjugate was used as coating antigen in this ELISA.

FIG. 3C, Competition ELISA assays were performed using the appropriate peptide for each antibody. Peptide-bovine serum albumin was used as coating antigen and free peptides were used as competing antigens.

FIG. 3D, Western blots of crude and gelatin-affinity purified type IV procollagenase. Shown are crude type IV procollagenase immunoblotted with A1-17 (20 μl of A2058 melanoma cell conditioned media, lane a), purified type IV collagenase immunoblotted with A1-17 (30 ng, lane b), purified type IV collagenase immunoblotted with A472-490 (30 ng, lane c).

FIG. 7 illustrates a time course for pAPMA activation of type IV procollagenase followed by gelatin zymogram and western blotting. 20 μl aliquots of A2058 melanoma cell conditioned media were activated in the presence of 1.0 mM pAPMA for the indicated times (min). The reactions were stopped by the addition of EDTA to 10 mM and the samples were electrophoresed on a 9% acrylamide gel with or without gelatin. The gelatin containing gels were developed as zymograms after electrophoresis. The nongelatin containing gels were electrophoretically transferred to nitrocellulose and then immunostained with the designated affinity purified antibodies (1 μg/ml). Loss of the amino terminal antigenic domain occurs during the pAPMA induced conversion from the 70 kDa to the 62 kDa form. MWM, prestained markers.

FIG. 10 illustrates the amino termini (residues 1-110) of type IV procollagenase (top line), interstitial procollagenase (middle line), and prostromelysin (bottom line). The area of homology just upstream from the cleavage site is shown in box A, the cleavage sites following pAPMA activation are shown in box B and the cysteine residues are underlined. Additional reported sites of cleavage following pAPMA treatment of interstitial collagenase and stromelysin are denoted by asterisks.

FIG. 12 illustrates a comparison of peptides tested for enzyme inhibitory activity. The peptides were derived from the amino terminal sequence shown in FIG. 10. The core sequence PRCG is necessary for inhibitory activity based on the fact that peptides lacking this sequence are devoid of significant inhibitory activity.

DETAILED DESCRIPTION OF THE INVENTION

It is the object of this invention to provide peptide sequences that have blocking activity against the metalloproteinase.

It is a further object of the invention to provide antibodies for use in identifying the presence of metalloproteinase.

It is a further object of this invention to provide a method of treating patients suffering tissue damage arising from tissue destruction caused by activated metalloproteinase.

Figure 2:
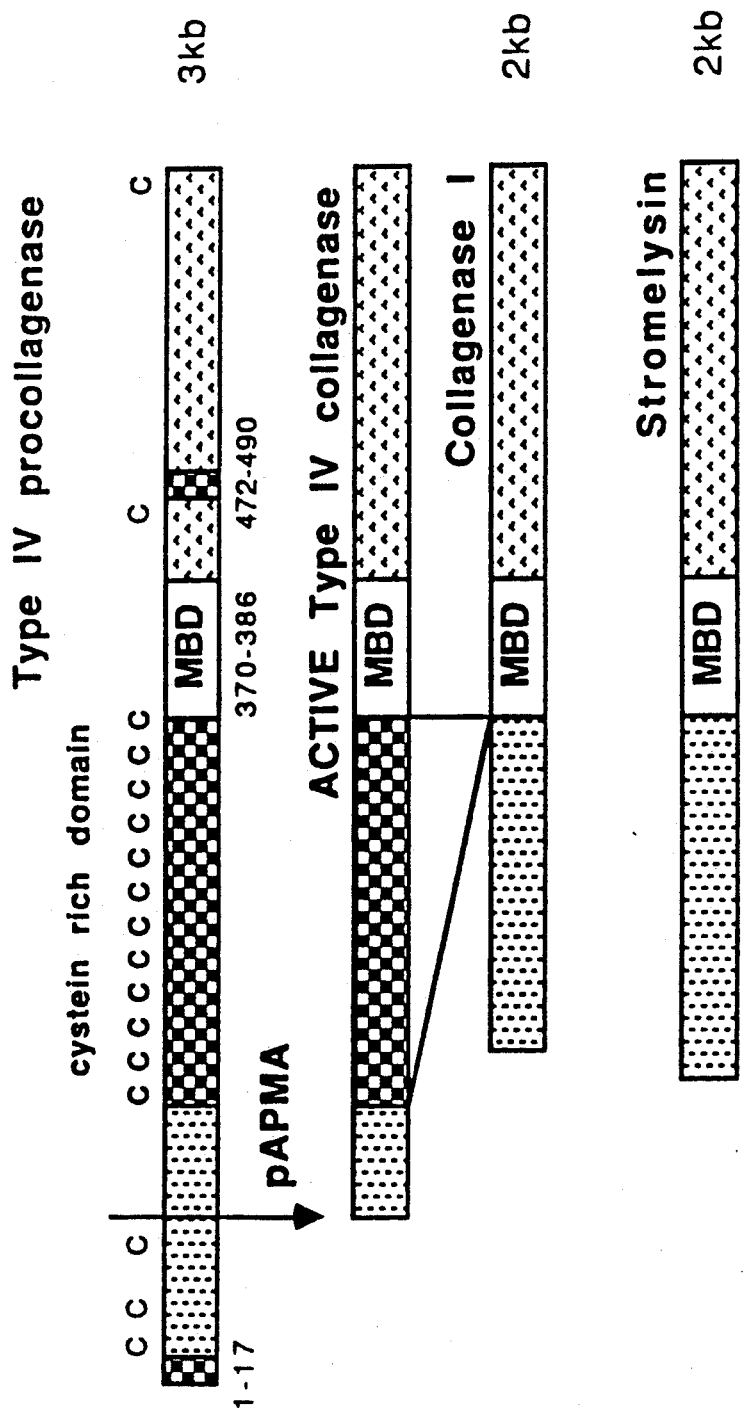
FIG. 2 illustrates a comparison of amino acid homologies between type IV procollagenase and prostromelysin and procollagenase I organized into domains.

Complete sequencing of the human type IV collagenase is illustrated in FIG. 1. This sequence reveals that this protein can be divided into a series of domains as shown in FIG. 2. A cysteine-rich (12 cysteine residues) domain encoded by a segment of approximately 1 kb has no significant homology with other sequenced metalloproteinases such as type I collagenase and stromelysin. The cysteine-rich region, however, does show significant homology to fibronectin. Three other domains of type IV collagenase show significant homologies with other metalloproteinases (FIG. 2). In particular, a region at residues 371 to 386, designated "MBD" and illustrated in FIG. 2, has closely homologous sequences in all three metalloproteinases including thermolysin. In the actual crystallized thermolysin, this region is related to the putative Zn binding domain of the enzyme. However, the MBD sequence or the cysteine-rich sequence has never previously been directly tested for its functional role in the metalloproteinase activity. In the present invention (a) synthetic peptides derived from these regions, and (b) affinity purified antibodies directed against these regions constitute inhibitors which block gelatinase and type IV collagenase activity. Furthermore, peptides derived from fibronectin homologous to the type IV collagenase domains outlined also inhibit binding of type IV collagenase to its substrates.

The synthetic peptide corresponding to residues 371-386 of type IV collagenase abolished the gelatinase and the collagenase type IV activity. This is demonstrated in FIG. 5 using gelatin zymograms. Furthermore, affinity purified antibodies recognizing these domains also inhibited the gelatinase and collagenase type IV activities. The mechanism of action of these peptides was, at least in part, due to their ability to complete for binding of type IV collagenase to type IV collagen (FIG. 6).

The metalloproteinase peptide inhibitor has a protein peptide having substantial homology with a histidine-containing domain at residues 371 to 386 of type IV collagenase. The protein peptide inhibits gelatinolytic and collagenolytic activities of metalloproteinases. The protein peptide of the metalloproteinase inhibitor preferably contains at least one histidine residue for activity. One desirable embodiment of the protein peptide of the metalloproteinase inhibitor has a histidine-containing sequence, said sequence being a member selected from the group consisting of VAAHEFGHAMGLEHSQ, VAAHEFGAAMGLEHSQ, VAA- HELGHSLGLSHST, VAAHEIGHSLGLFHSA, VVAHELTHAVTDYTAG and the fibronectin peptide AAHEEICTTNEGVM. Since the latter peptide was effective and required the histidine residue, the core sequence AHE was determined to be a minimum determinant of one major embodiment of the invention. Peptides derived from the cysteine-rich region (residues 200-370) also inhibited enzyme substrate binding and are considered additional embodiments of the invention.

Figure 5:
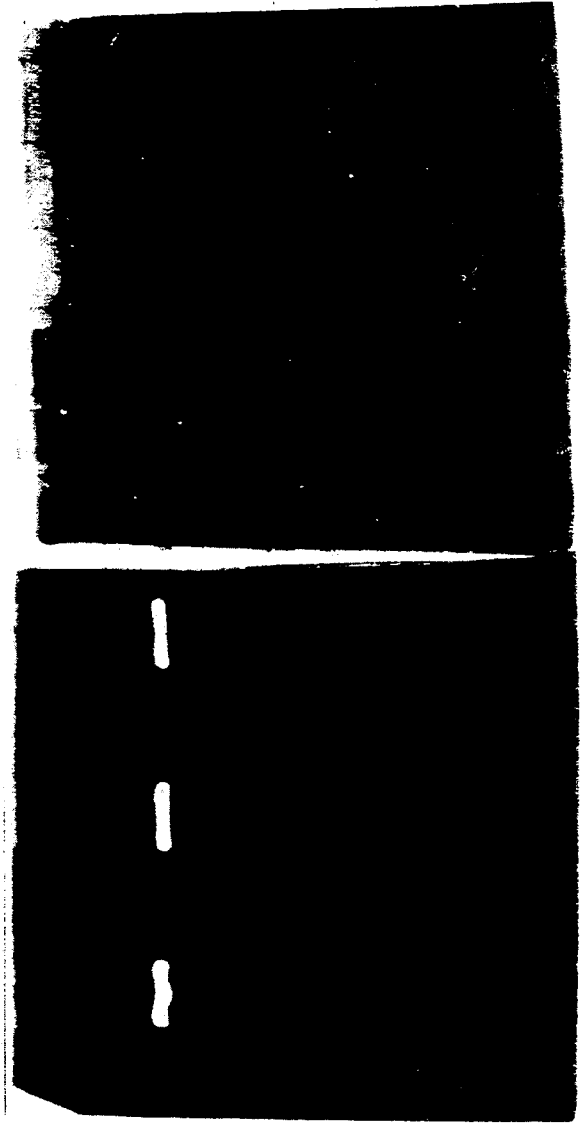
FIG. 5 illustrates the gelatin zymogram inhibition of type IV collagenase by the designated synthetic peptides. The gelatinase activity is visualized as white cleared bands at approximately 70 kDa. The white cleared bands are abolished in the presence of the inhibitor. Three replicates are shown.
Figure 6:
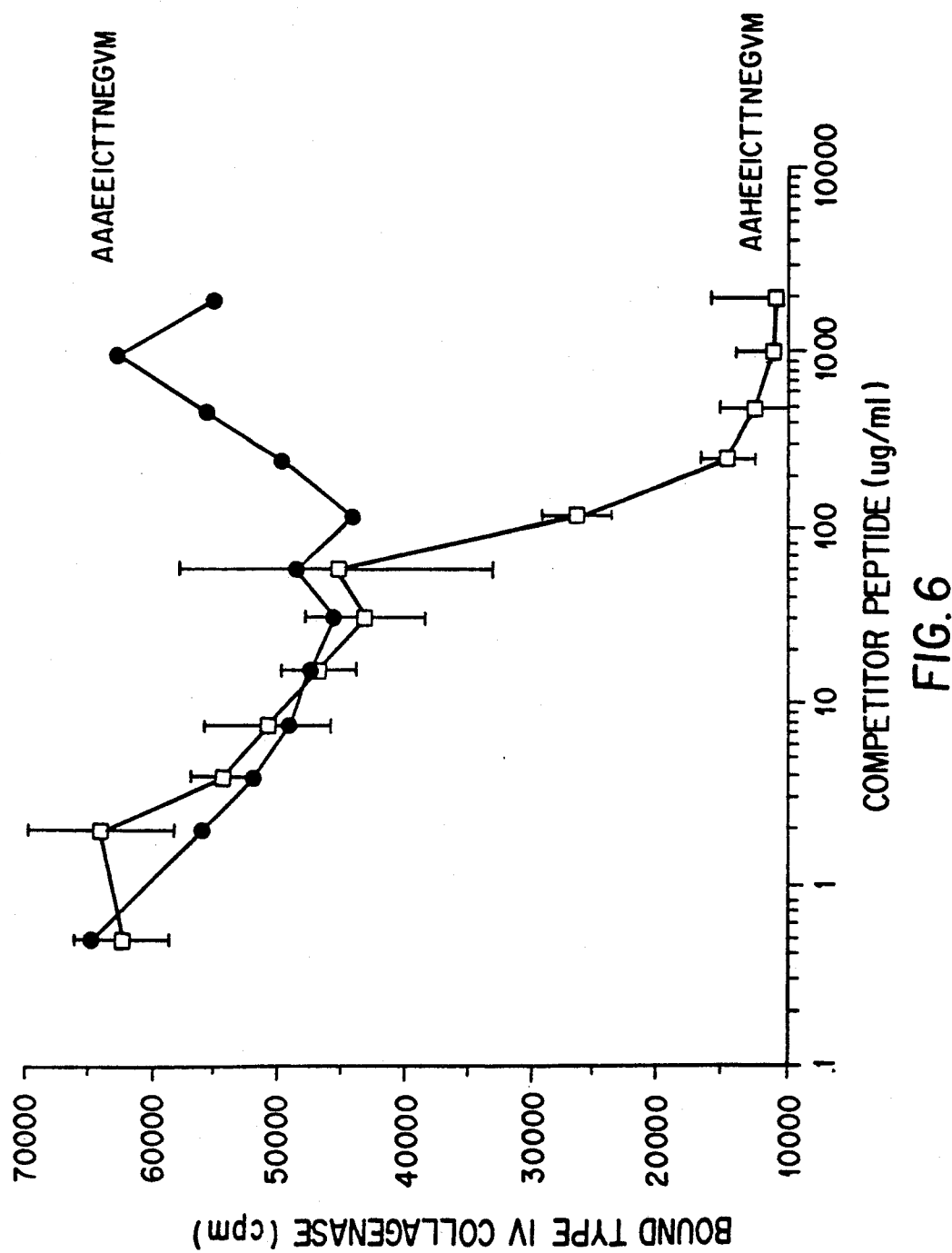
FIG. 6 illustrates an example inhibition of binding of labeled type IV collagenase to type IV collagen by the designated peptides. The histidine containing peptide is derived from a region in fibronectin homologous to the histidine containing domain of type IV collagenase shown in FIGS. 2 and 5. The histidine residue is required for binding competition.

By substituting amino acids into conserved residue regions, it was demonstrated that the histidine residues were, in part, required for the inhibitory activity of the peptide as shown in FIGS. 5 and 6. When all three histidines were replaced with alanines, the peptide was completely inactive. However, if only the central histidine was replaced by alanine, the inhibitory activity was retained. Furthermore, replacement of the two glutamic acid (E) residues with glutamine (Q) substantially altered the inhibitory activity of the peptide. These inhibitory peptides bear no homology to the cleavage site on the type IV collagen or gelatin substrate. Their mechanism of action involves an interference of the enzyme-substrate interaction in a region of the proteinase which can interact with a metal ion, such interaction being necessary for substrate cleavage. The active peptide partially inhibited the gelatinolytic activity of thermolysin under concentrations of the peptide which abolished the type IV collagenase activity. The active peptides failed to inhibit a variety of serine and thiol proteases or "non-metalloproteinases" tested, including plasmin and trypsin.

Table 1 is a list of the synthetic peptides, prior to substitution, chosen from the sequence in FIG. 1, based on functional studies by the inventors and based on homology comparisons with other metalloproteinases.

TABLE 1

List of Peptides Synthesized Derived from Type-4 Collagenase, N—C

1. Ala—Pro—Ser—Pro—Ile—Ile—Lys—Phe—Pro—Gly—Asp—Val—Ala—Pro—Lys—Thr—Asp—Lys
2. Glu—Leu—Ala—Val—Gln—Tyr—Leu—Asn—Thr—Phe—Tyr—Gly—Cys—Pro—Lys
3. Asn—Thr—Phe—Tyr—Gly—Cys—Pro—Lys—Glu—Ser—Cys—Asnm—Leu—Phe—Val—Leu—Lys
4. Glu—Ser—Cys—Asn—Leu—Phe—Val—Leu—Lys—Asp—Thr—Leu—Lys—Met—Gln—Lys
5. Phe—Phe—Gly—Leu—Pro—Gln—Thr—Gly—Asp—Leu—Asp—Gln—Asn—Thr—Ile—Glu
6. Thr—Met—Arg—Lys—Pro—Arg—Cys—Gly—Asn—Pro—Asp—Val—Ala—Asn
7. Thr—Met—Arg—Lys—Pro—Arg—Cys—Gly—Asn—Pro—Asp—Val—Ala—Asn—Tyr—Asn—Phe—Phe—Pro—Arg—Lys—Pro—Lys
8. Arg—Lys—Pro—Arg—Cys—Gly—Asn
9. Asn—Pro—Asp—Val—Ala—Asn—Tyr—Asn—Phe—Phe—Pro—Arg—Lys—Pro—Lys—Trp—Asp—Lys—Asn—Gln
10. Met—Ile—Asn—Phe—Gly—Arg—Trp—Glu—His—Gly
11. Lys—Tyr—Gly—Phe—Cys—Pro—Glu—Thr—Ala
12. Met—Ser—Thr—Val—Gly—Gly—Asn—Ser—Glu—Gly—Ala
13. Met—Trp—Cys—Ala—Thr—Thr—Ala—Asn—Tyr—Asp—Asp—Arg—Lys—Trp—Gly—Phe—Cys—Pro—Asp—Gln—Gly—Tyr—Ser—Leu
14. Val—Ala—Ala—His—Glu—Phe—Gly—His—Ala—Met—Gly—Leu—Glu—His—Ser—Gln
15 Ala—Ala—His—Glu
16. Asp—Lys—Pro—Met—Gly—Pro—Leu—Leu—Val—Ala—Thr—Phe—Trp—Pro—Gln—Leu—Pro—Glu—Lys Peptides Tested for Inhibition of Type-4 Collagenase Binding or Activity 1. Val—Ala—Ala—His—Glu—Phe—Gly—His—Ala—Met—Gly—Leu—Glu—His—Ser—Gln
2. Val—Ala—Ala—Ala—Glu—Phe—Gly—Ala—Ala—Met—Gly—Leu—Glu—Ala—Ser—Gln
3. Val—Ala—Ala—His—Glu—Phe—Gly—His—Ala—Met—Gly—Leu—Glu—His—Ser—Gln
4. Val—Ala—Ala—His—Glu—Phe—Gly—Ala—Ala—Met—Gly—Leu—Glu—His—Ser—Gln
5. Val—Ala—Ala—Ala—Glu—Phe—Gly—His—Ala—Met—Gly—Leu—Glu—His—Ser—Gln
6. Val—Ala—Ala—Ala—Glu—Phe—Gly—Ala—Ala—Met—Gly—Leu—Glu—His—Ser—Gln
7. Val—Ala—Ala—His—Glu—Phe—Gly—Ala—Ala—Met—Gly—Leu—Glu—Ala—Ser—Gln
8. Val—Ala—Ala—His—Ala—Phe—Gly—His—Ala—Met—Gly—Leu—Ala—His—Ser—Gln
9. Val—Val—Ala—His—Glu—Leu—Thr—His—Ala—Val—Thr—Asp—Tyr—Thr—Ala—Gly
10. Val—Ala—Ala—Glu—Lys—Phe—Gly—Glu—Ala—Met—Gly—Leu—Lys—Glu—Ser—Gln
11. Ala—Ala—His—Glu
12. Ala—Ala—His—Glu—Glu—Ile—Cys—Thr—Thr—Asn—Glu—Gly—Val—Met
13. Ala—Ala—Ala—Glu—Glu—Ile—Cys—Thr—Thr—Asn—Glu—Gly—Val—Met
14. Thr—Met—Arg—Lys—Pro—Arg—Cys—Gly—Asn—Pro—Asp—Val—Ala—Asn—Tyr—Asn—Phe—Phe Pro—Arg—Lys—Pro—Lys
15. Thr—Met—Arg—Lys—Pro—Arg—Cys—Gly—Asn—Pro—Asp—Val—Ala—Asn
16. Thr—Met—Arg—Lys—Pro—Arg—Ser—Gly—Asn—Pro—Asp—Val—Ala—Asn
17. Arg—Lys—Pro—Arg—Cys—Gly—Asn
18. Glu—Ser—Cys—Asn—Leu—Phe—Val—Leu—Lys—Asp—Thr—Leu—Lys—Met—Gln—Lys

TABLE 1-continued

19. Met—Trp—Cys—Ala—Thr—Thr—Ala—Asn—Tyr—Asp—Asp—Arg—Lys—Trp—Gly—Phe—Cys—Pro—Asp—Gln—Gly—Tyr—Ser—Leu

EXAMPLE 1

Histidine Containing Peptide Inhibitor

Methods

Gelatin Zymogram

A gelatin zymogram for visualizating gelatinase activity was prepared using the stock solutions and mixing procedures below.

| Stock Solutions: | Mixing Procedures: |
|---|---|
| a) 2 M Tris HCl, pH 8.8 | 242 g Tris base in 800 ml of dH$_2$O, adjust pH to 8.8 with concentrated HCl and dilute to 1 liter |
| b) 0.5 M Tris HCl, pH 6.8 | 6.05 g Tris base in 80 ml of dH$_2$O, adjust pH to 6.8 with concentrated HCl and dilute to 100 ml |
| c) 30% Acrylamide with 0.8% bisacrylamide | To 100 g of acrylamide, add 2.4 g of bisacrylamide, add enough dH$_2$O to dissolve acrylamide. Dilute to 333 ml and store at 4° C. in an aluminum foil wrapped bottle |
| d) 10% SDS | Dissolve 100 g of SDS in dH$_2$O and dilute to 1 liter final volume |
| e) 10% Ammonium persulfate | To 1 g of ammonium persulfate, add dH$_2$O to 10 ml final volume. Store at 4° C. |
| f) 10 X Electrode buffer | Dissolve 144 g glycine in 600 ml of dH$_2$O, add 125 ml of 2 M Tris HCl, pH 8.8, and 100 ml of 10% SDS. Dilute to final volume of 1 liter |
| g) 5 X Sample buffer | Dissolve 50 mg bromophenol blue in 2.5 ml of 0.5 M Tris HCl, pH 6.8, add 4 ml 10% SDS, 2.5 ml of glycerol and store at 4° C. |
| h) TEMED | |
| i) 1% Gelatin | Dissolve 1 g of gelatin in 100 ml of dH$_2$O by warming suspension under running hot tap water |
| j) Gel staining solution | 30% methanol, 10% acetic acid, 0.1% amido black 10 B |
| k) Destaining solution | 30% methanol, 10% acetic acid |

Procedure

The procedure for preparing the gelatin zymogram used for this example utilized the following steps and reagents.

1) Assemble gel forming apparatus.
2) Prepare resolving gel solution for polymerization: 9% acrylamide 40 ml final volume
in a 50 ml falcon tube
12 ml 30% acrylamide, 0.8% bisacrylamide
0.4 ml 10% SDS
7.5 ml 2M Tris HCl, pH 8.8
4 ml 1% gelatin
16 ml dH$_2$O
3) After mixing, add 0.4 ml 10% ammonium persulfate and mix again.
4) Initiate polymerization with 40 μl of TEMED, mix and pour 32 ml of gel solution into the gel form.
5) Overlay solution with water saturated butanol and allow 30-45 minutes to polymerize.
6) After polymerization, wash gel surface with dH$_2$) and allow to dry.
7) Prepare stacking gel solution for polymerization: 3% acrylamide 10 ml final volume
to a 15 ml falcon tube add
2.5 ml 0.5M Tris HCl, pH 6.8
0.1 ml 10% SDS
1.0 ml 30% acrylamide, 0.8% bisacrylamide
0.1 ml 10% ammonium persulfate
5.3 ml dH$_2$O
8) Initiate polymerization of stacking gel with 40 μl TEMED and mix.
9) Pour approximately 6 ml into gel form over polymerized running gel and insert well comb.
10) Remove air bubbles from the bottom of the comb teeth and add additional gel solution, if needed.
11) Allow stacking gel to polymerize 15-20 min.
12) After polymerization, remove comb from stacking gel and add 1 X electrode buffer to both electrode chambers.
13) Remove air bubbles from sample wells and bottom of gel.
14) Load samples and run electrophoresis at 30 mamps/gel.
15) After completion of electrophoresis, wash gel in two changes of 2.5% Triton X-100 for 60 minutes with gentle agitation at room temperature.
16) Discard Triton X-100 solution and place gel in 1 X collagenase buffer, incubate at 37° C. for 2-4 hours or overnight at room temperature.
17) After incubation period, stain gel for 30 minutes in 0.1% amido black and then destain for approximately 90 minutes.
18) Zones of clearing correspond to gelatinolytic activity.

The preparation of separating gels of various concentrations are shown below.

| | 40 ml final volume | | | |
|---|---|---|---|---|
| | 6% | 8% | 9% | 10% |
| 30% acrylamide, 0.8% bis | 8 ml | 10.6 ml | 12 ml | 13.3 ml |
| dH$_2$O | 20 ml | 17.4 ml | 16 ml | 14.7 ml |

Soluble Collagenase Assay

The procedure for the collagenase assay of this example utilized the following preparation.

A 10 X collagenase buffer was prepared to obtain final concentrations of 0.5M Tris, 2.0M NaCl, 0.05M CaCl$_2$, 2% Brij 35. To prepare 1 liter, combine
60.55 g Tris
116.88 g NaCl
7.35 g CaCl$_2$
20 g Brij 35
Then dissolve in 800 ml of dH$_2$O and adjust the pH to 7.6 with the addition of concentrated HCl. Adjust the final volume to 1 liter and filter sterilize.

A 10 X bacterial collagenase (positive control) was prepared to obtain a final concentration of 0.5% (w/v). This involved the dissolving of 10 mg of bacterial collagenase (Sigma #C-5138) in 2 ml of 1 X collagenase buffer and storing at −20° C. in 100 ml aliquots.

A bovine serum albumin (carrier protein) solution was prepared to obtain a final concentration of 0.5% (w/v) bovine serum albumin in 1 X collagenase buffer. This involved the dissolving of 100 mg of bovine serum albumin in 20 ml of 1 X collagenase buffer and storing aliquoted in 1 ml fractions at −20° C.

A trichloroacetic acid-tannic acid-proline solution (TCATAP) was prepared to obtain a final concentration of 10% TCA, 0.5% tannic acid, 2 mM proline. This involved the combining of 10 ml of 100% trichloroacetic acid solution, 10 ml of 5% tannic acid solution and 1 ml of 200 mM proline solution, diluting to 100 ml final volume and store at 4° C., and replacing this solution every 4 weeks.

Procedure

1. Place enzyme sample activator (usually 1 mM pAPMA) and test solution in 1.5 ml Eppendorf tube. Combined volume must equal 60 $\mu$l. Add 1 X collagenase buffer, if necessary. If necessary, preincubate.

2. Prepare type IV collagen substrate by diluting stock $^3$H-type IV collagen (NEN #NET-931 lot #2511-018) 1:120 with 1 X collagenase buffer. Heat to 55° C. for 10 minutes and cool on ice.

3. Add 5 $\mu$l of diluted $^3$H-type IV collagen solution to each assay tube. Vortex to mix and incubate at 28° C. for 4 hours.

4. At the end of the incubation period, add 2 $\mu$l of carrier BSA solution and 7 $\mu$l of TCATAP solution. Vortex mix and allow to stand on ice for at least 10 minutes.

5. Pellet the precipitate by centrifuging in the microfuge for 10 minutes with the speed set at 6. Orient the tubes when placing them in the microfuge in order that the position of the pellet will be known.

6. Immediately after centrifugation, aspirate 55 $\mu$l of the supernatant and place in a scintillation vial. Add 5 ml of scintillation cocktail, shake well and count.

The amino terminal sequence of A2058 melanoma cell type IV procollagenase (residues 1-17, APSPIIKFPGDVAPKTD) as well as that of an internal domain (residues 472-490, DKPMGPLLVATFNPELPEK) were synthesized for use in preparation of monospecific antibodies. These peptides were chosen because they were obtained in the direct sequencing of the enzyme (17,19), were confirmed in the predicted sequence from the cDNA clone (17), and are derived from regions which do not show homology with the other metalloproteinases. The affinity purified antibodies were characterized using direct ELISA as well as competition experiments. The antibodies showed no cross reactivity with bovine serum albumin or unrelated peptides. The affinity purified antibodies are capable of immunoprecipitating the type IV procollagenase (19). Western blots demonstrated that both antibodies recognized the type IV procollagenase as a single band in A2058 conditioned media identical to the Western blotting with the purified type IV collagenase.

Figure 8:
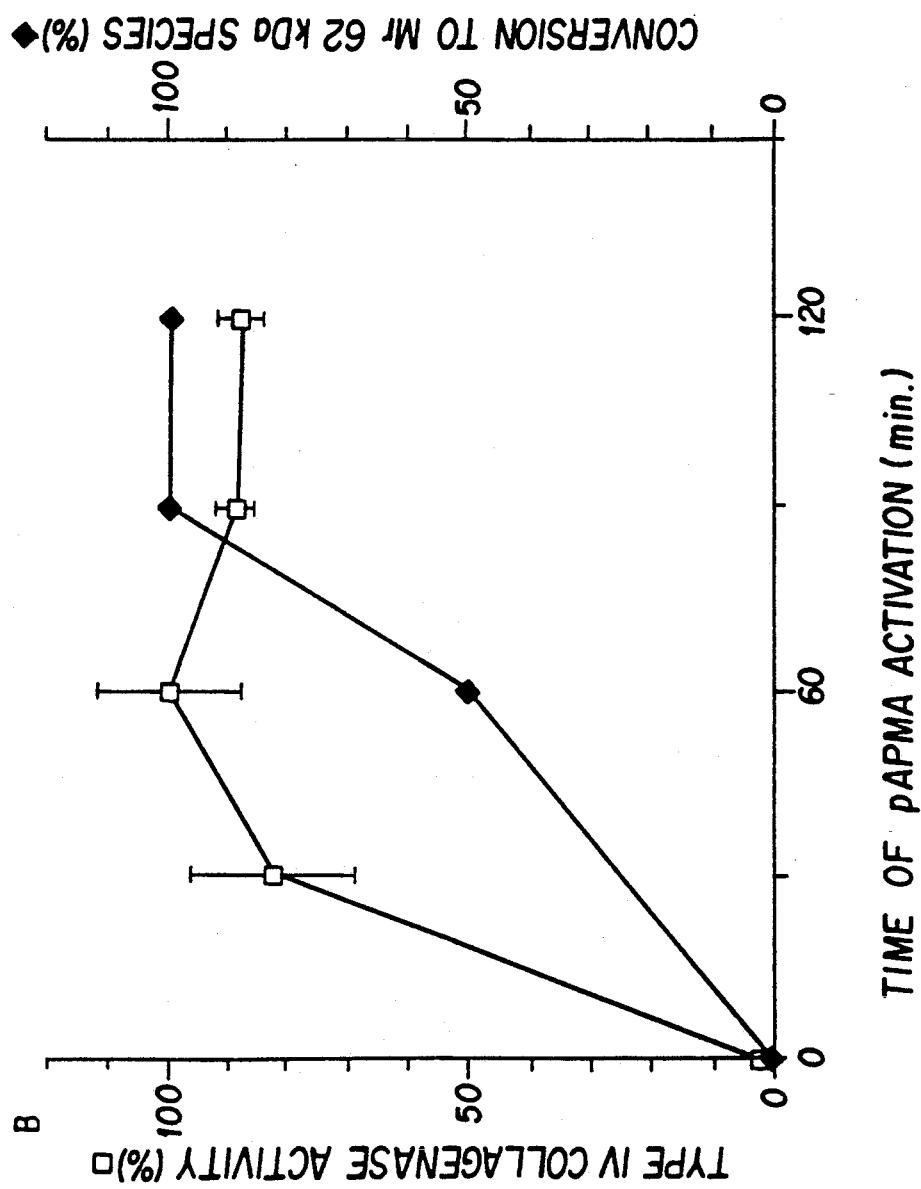
FIG. 8 illustrates a time course of pAPMA activation of purified type IV collagenase followed by type IV collagen degradation assay. 10 μl aliquots of purified type IV collagenase (23 μg/ml) were made 1 mM in pAPMA and preincubated at 37° C. for the indicated times. The samples were then diluted to 60 μl final volume by the addition of 50 mM Tris HCl, 0.15M NaCl, 5 mM CaCl₂, pH 7.6. $^3$H-type IV collagen (New England Nuclear) was added and the reaction mix allowed to incubate at 37° C. for 30 min. Samples were assayed in triplicate. Maximal activity corresponds to 2.8 μg type IV collagen degraded/h/μg purified enzyme at 37° C.

The time course for pAPMA activation was followed using gelatin zymogram analysis, type IV collagenase assays and both affinity purified antibodies on immunoblots (FIG. 7). Gelatin zymogram (FIG. 7) analysis of A2058 melanoma cell type IV collagenase revealed a single band of gelatinolytic activity with a molecular weight of 70 kDa daltons. Incubation at 37° C. in the presence of 1 mM pAPMA resulted in gradual conversion of this band of gelatinolytic activity to a lower molecular mass of 62 kDa. This conversion was completely inhibited in the presence of 10 mM EDTA and did not occur in the absence of added pAPMA (not shown). Type IV collagenase assays of the purified type IV procollagenase revealed no collagenolytic activity in the absence of the organomercurial compound pAPMA during the incubation period. The enzyme could be activated by preincubation with pAPMA. The time course of activation during preincubation with pAPMA as measured by collagenase assay shows that full collagenolytic activity is obtained rapidly (FIG. 8). Antibody A472-490 demonstrated a time dependent reduction in molecular weight with incubation that corresponds to that seen in the gelatin zymograms (FIG. 7). This conversion appeared 50% complete by the 60 minute time point and essentially complete by the 90 minute. Antibody A1-17 corresponding to the amino terminal epitope showed a direct reduction in immunostaining during the course of pAPMA activation. These results indicate that the apparent molecular weight reduction following conversion of the latent to a stable, active collagenase with the organomercurial compound is the result of the loss of an amino terminal peptide fragment.

Figure 3A:
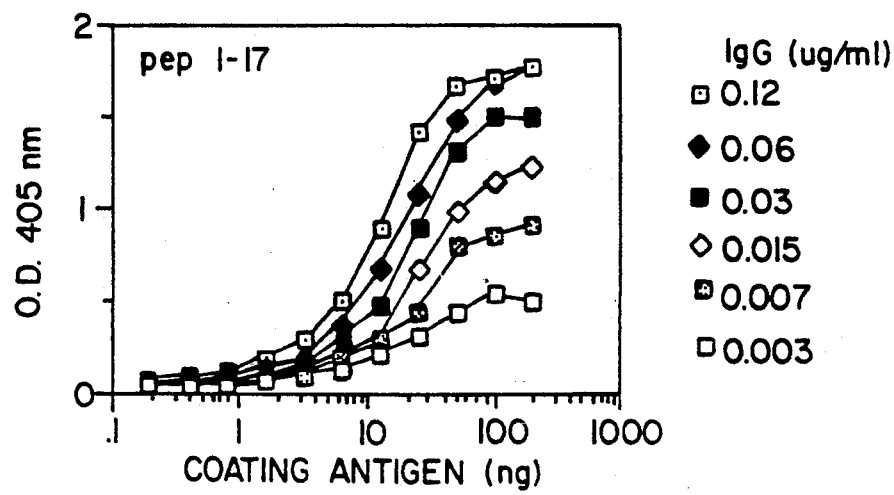
Figure 9:
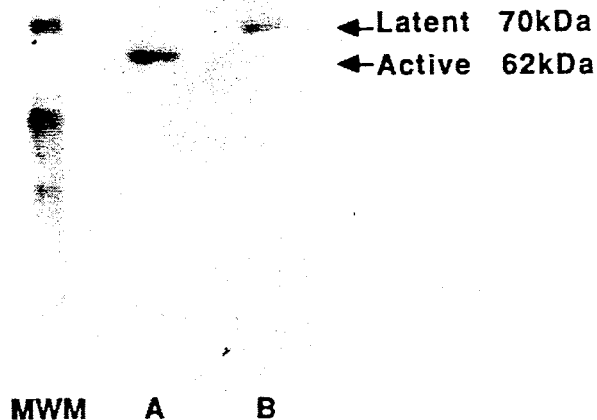
FIG. 9 illustrates the amino acid sequences of the latent and active forms of type IV procollagenase as determined by direct amino acid sequencing of the purified enzyme. Also shown is the cleavage site of the autocatalysis on pAPMA activation. The insert shows the apparent molecular weights on a silver stained NaDodSO₄-PAGE gel of the purified latent (20 ng, lane A) and active enzymes (20 ng, lane B).

Gelatin-affinity purified type IV procollagenase was further purified by reverse phase HPLC both before and after pAPMA activation. The chromatograms showed essentially no change in the retention times for the latent and active forms. When the peaks were collected and analyzed by NaDodSO$_4$-PAGE, the procollagenase peak prior to pAPMA activation showed a single band at approximately 70 kDa under non-reducing conditions (FIG. 9, insert). The collagenase peak after pAPMA activation (16 hours, 37° C.) showed a single band at 62 kDa under non-reducing conditions (FIG. 3A).

The material obtained from the procollagenase peak on HPLC prior pAPMA activation was subjected to direct amino acid sequencing. This material gave an amino terminal sequence that was identical to that previously determined for this enzyme (FIG. 9). Direct sequencing of the pAPMA activated material, after HPLC purification, revealed a single new amino terminal sequence (FIG. 9). This definitively demonstrates that pAPMA activation is accompanied by an autocatalytic removal of an amino terminal peptide fragment from the latent enzyme with a reduction in the molecular mass of about 8 kD. This cleavage occurs at only a single site as no evidence of any other amino terminal amino acids were detected upon sequencing many preparations of the purified, activated enzyme and no evidence of intermediates were detected by Western blotting or gelatin zymogram analysis.

The results of this study demonstrate that type IV collagenase is secreted in a latent proenzyme form requiring activation before obtaining collagenolytic activity. The organomercurial compound pAPMA is capable of this activation. Organomercurial activation of type IV procollagenase is accompanied by conversion of the proenzyme form to a lower molecular weight, active enzyme form by removal of an 80 amino acid residue peptide fragment from the amino terminus. Maximum collagenolytic activity is obtained rapidly following exposure to pAPMA. The attainment of this activity prior to complete conversion to the stable lower molecular weight form is consistent with a conformational rearrangement in the zymogen form that results in an active but unstable species, as has been reported for interstitial collagenase and stromelysin (1,26). Activation occurs with highly purified type IV procollagenase enzyme. Thus, the activation in the presence of the organomercurial compound is autoproteolytic since pAPMA is itself incapable of peptide bone hydrolysis. This autocatalytic mechanism of activation with organomercurial compounds has been demonstrated for other extracellular matrix degrading metalloproteinases, such as interstitial collagenase (5,25), and stromelysin (22,25,26,27). These three metalloproteinases, type IV procollagenase, interstitial procollagenase and prostromelysin show significant homology at the amino acid level (5,17,22,23,25,27).

When the amino acid sequences for the amino termini of these enzymes are aligned for maximum homology (FIG. 10), two correlations are observed. First, the site of autoproteolysis in type IV collagenase upon activation with pAPMA, which result in a stable, active enzyme, occurs at an identical locus to that previously reported for prostromelysin activation and the major product of collagenase activation (25,26). Similar sites of autoproteolysis following pAPMA treatment have been reported by others for prostromelysin (22) and interstitial procollagenase (5). Second, the amino terminal peptide fragments which are removed during activation of all three enzymes contain an odd number of cysteine residues. In type IV procollagenase, three cysteine residues are present in the removed peptide fragment; Cys-31, Cys-36 and Cys-73. In interstitial procollagenase and prostromelysin, there is a single cysteine residue present in the removed peptide fragment that corresponds to Cys-73 in type IV procollagenase. Thus, the conversion from an odd number of cysteine residues in the latent metalloproteinases to an even number of cysteine residues in the pAPMA activated form, appears to be a common feature in all three enzymes. The removal of an unpaired cysteine may be of functional significance. Finally, all three enzymes contain a highly conserved region immediately upstream to the activation locus consisting of the amino acid sequence PRCGVPDV. This sequence contains the unpaired cysteine residue in the propeptides of interstitial collagenase and stromelysin (25) and by homology the unpaired cysteine (out of the three present) in the type IV collagenase propeptide. A recent report has shown by site-directed mutagenesis studies of rat transin (homolog of human stromelysin), the importance of this conserved region in the autoactivation of this family of metalloproteinases. Recombinant transin forms containing mutations in this sequence showed a higher rate of spontaneous activation when compared with the native sequence (27).

It was discovered that type IV collagenase proenzyme activation by an organomercurial compound, pAPMA, is accompanied by an autocatalytic removal of an 80 amino acid amino terminal fragment, resulting in a stable, active enzyme species of 62 kDa. Furthermore, these data show that type IV collagenase shares not only sequence homology but functional domain identity with the amino terminal regions of other extracellular matrix degrading metalloproteinases.

Figure 11:
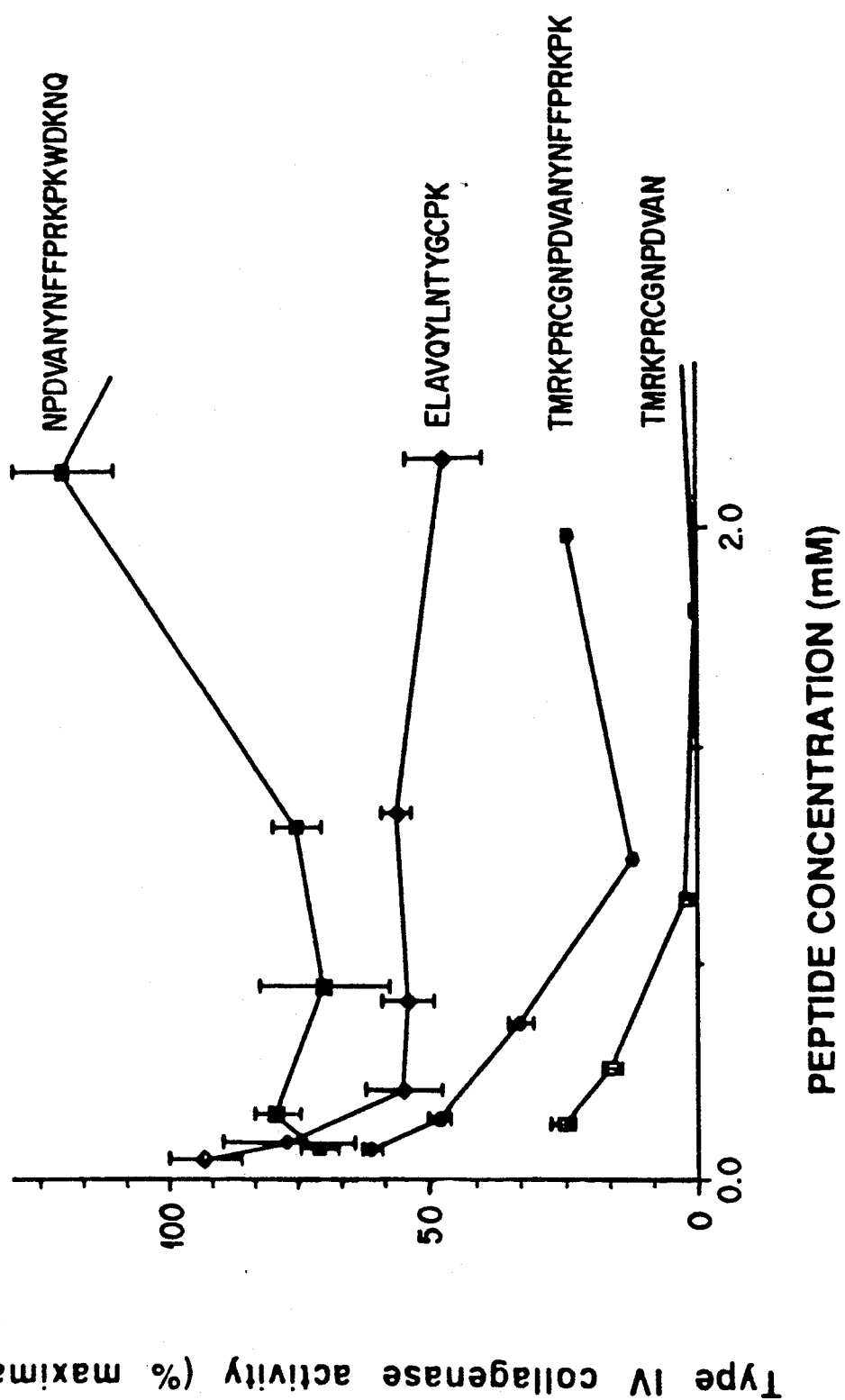
FIG. 11 illustrates the dose dependent inhibition of purified activated type IV collagenase cleavage of pepsinized type IV collagen by the designated synthetic peptides. Peptide TMRKPRCGNPDVAN at a concentration of 0.1 mM inhibits 80% of the enzyme activity. Higher concentrations abolish all enzyme activity.

As shown in FIGS. 8 and 9, an amino terminal peptide (residues 1-80) is cleaved off during type IV collagenase activation. This raised the possibility that this peptide contains an intrinsic enzyme inhibitor which blocks the active site and renders the enzyme inactive. Removal of this amino terminal segment during activation thus removes this inhibitor and exposes the active site. The critical region involved in the inhibition is the region enclosed in a box in FIG. 10 which contains an unpaired cysteine residue. This region shows a conserved nature in the other metalloproteinases, it has a high probability of beta turn conformation by Chou Faseman analysis. Furthermore, it was reasonable to hypothesize that the unpaired cysteine residue in this sequence interacted in a non-covalent fashion with the metal ion in the active site of the enzyme. Organomercurial activation (it is known that APMA binds to sulfhydryl residues) would thus disrupt this interaction and cause a conformational change which would separate the inhibitor segment from proximity to the active site. To test this completely novel hypothesis, synthetic peptides were prepared which corresponded to a series of overlapping regions in the amino terminal residues 1-87. As shown in FIGS. 11 and 12, only those peptides incorporating the conserved region containing the unpaired cysteine were strongly inhibitory at concentration less than 0.1 mM. The cysteine was required for the activity. These peptides, therefore, constitute a highly novel class of inhibitors for metalloproteinases.

EXAMPLE 2

Cysteine Containing Peptide Inhibitors

Methods

Culture Methods

Human A2058 melanoma cells were grown to 80% confluence in DMEM with 10% fetal bovine serum. The media was then replaced with serum-free DMEM and the culture continued for 24 hours. The serum-free conditioned media was collected and concentrated by ultrafiltration (Amicon YM 30 membrane) prior to storage at $-20°$ C.

Purification of Type IV Procollagenase

Type IV procollagenase was purified directly from human A2058 melanoma cell concentrated conditioned media by gelatin-Sepharose (Sigma) affinity chromatography in 0.05M Tris HCl, 0.005M $CaCl_2$, 0.5M NaCl, pH 7.6 buffer (TCS buffer) containing 0.02% Brij 35 (Sigma). The enzyme was eluted using TCS buffer containing 0.02% Brij plus 7% dimethyl sulfoxide. The sample was then concentrated and stored in the same buffer at $-70°$ C. until use. Type IV procollagenase was further purified by reverse-phase HPLC prior to amino acid sequence analysis on a Dionex A1400 system equipped with a 0.46 X 10 cm RP300 column (Pierce Co.) equilibrated in 0.1% trifluoroacetic acid. The column was eluted with a linear gradient to a 60% acetonitrile.

Preparation of Antibodies to Synthetic Peptides

The peptides used in the immunization procedures were synthesized on a Biosearch 9600 peptide synthesizer. Antibodies were prepared and purified as described for Example 3. The antibody preparations were characterized by ELISA using a commercial ELISA kit (Kirkegaard and Perry Laboratories) Immulon 2 plates (Dynatech, Inc.) as shown in FIGS. 3A, 3B, 3c, and 3D.

Activation of Type IV Procollagenase by Organomercurials

Stock solutions of 0.01M p-APMA in 0.05N NaOH were prepared fresh daily. Proenzyme samples were incubated with a final concentration 0.5 or 1.0 mM p-APMA for varying times (0-16 hours) at $37°$ C. Following incubation, the samples were analyzed directly by $NaDodSO_4$-PAGE on 9% acrylamide gels containing 0.1% gelatin (gelatin zymogram). Alternatively, the samples were run on 9% $NaDodSO_4$-PAGE and electroblotted onto Immobilon P membranes (Millipore).

Assays for Type IV Collagenolytic Activity

Type IV collagenase activity was assayed in the presence of inhibitory peptides as described for Example 1. The substrate used was ³H-propionylated, human type IV collagen (New England Nuclear). The reactions were carried out at 28° C. for 4 to 16 hours.

Figure 3B:
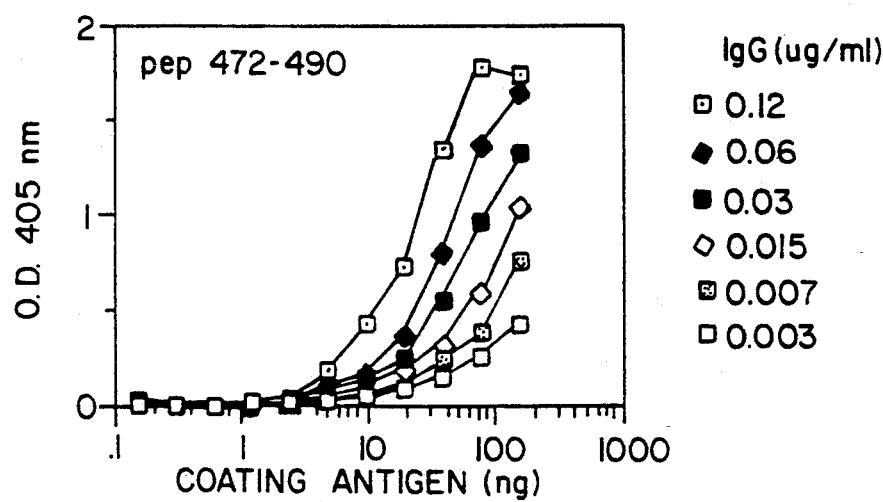
Figure 3C:
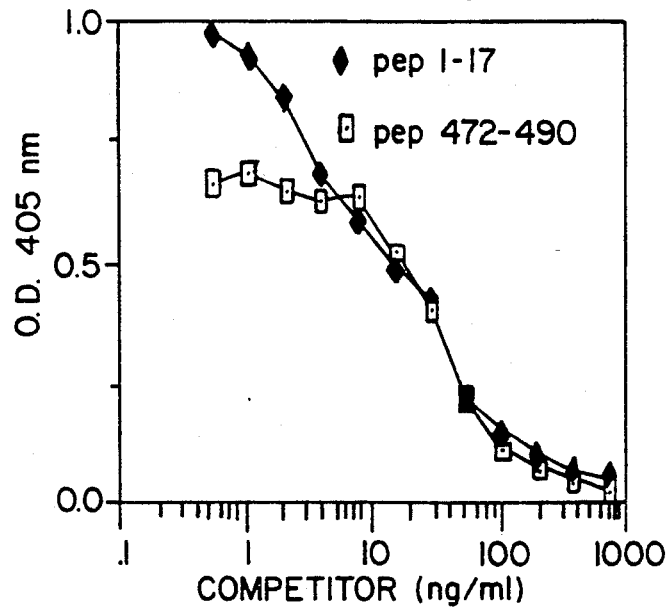
Figure 4A:
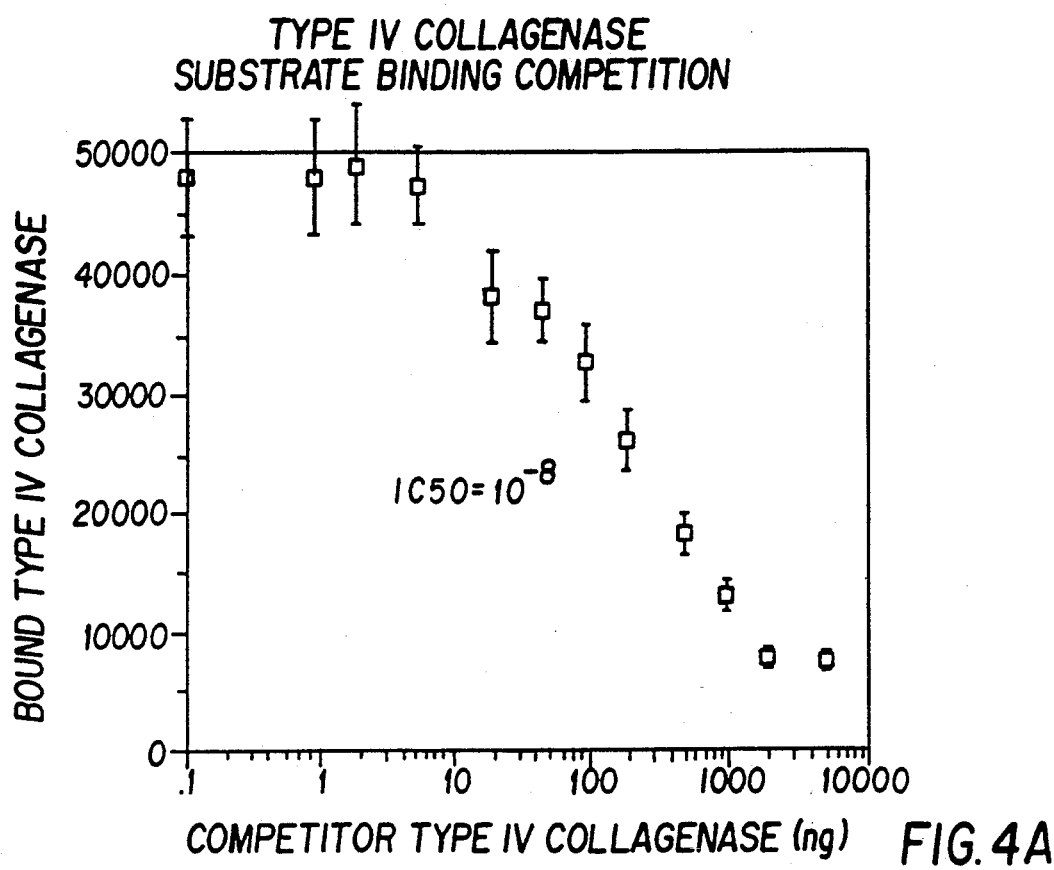
FIGS. 4A and 4B illustrate the assay for type IV collagenase binding to its substrate type IV collagen. Purified type IV collagenase was used to compete for the binding of labeled type IV collagenase to pepsinized type IV collagen coated in microtiter wells (mean±S.D.). Saturation of binding is demonstrated in the lower curve using increasing amounts of substrate.
Figure 4B:
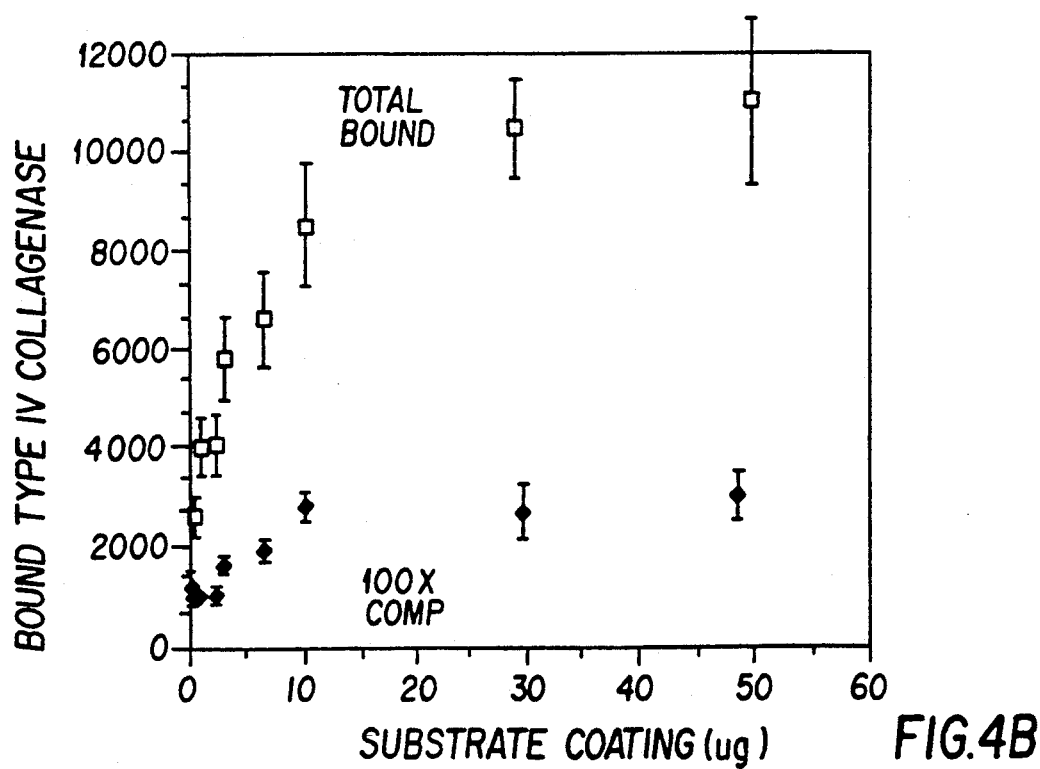

Type IV collagenase is a metalloproteinase which cleaves type IV collagen in a pepsin resistant domain. Organomercurial activation of the latent 70 kDa type IV collagenase (type IV procollagenase) results in the autocatalytic removal of an amino terminal domain resulting in the conversion to a 62 kDa activated form of the enzyme. Synthetic peptides corresponding to a series of domains extending from the amino terminus (residues 1-17), to an internal domain near the carboxy terminus (residues 472-490) (FIG. 1, Table 1) were used as antigens to generate affinity purified polyclonal antibodies which recognized their respective domains on the native type IV procollagenase. Enzyme-linked immunosorbant assays (ELISA) were used to demonstrate that antibody binding to solid phase synthetic peptides could be competed by solution phase peptides, and that each affinity purified antibody was monospecific (FIG. 3). Western immunoblotting studies of the time course of organomercurial activation process demonstrated that the antibodies recognized the solid phase enzyme in purified form, or among a complex mixture of proteins secreted by tumor cells in culture (FIGS. 3A, 3B, 3C, and 3D). Western blotting also indicated a direct loss of the amino terminal domain (residues 1-80) during the conversion to the lower molecular weight form (FIG. 7). Thus, antibodies which recognize peptide domains in the first 1-80 amino terminal residues could be used to distinguish the latent from the active form of the enzyme. Antibodies recognizing peptides in Table 1 were demonstrated to be useful in solid phase or solution phase direct or competition immunoassays to detect type IV collagenase antigen in human serum and human urine. Such body fluid assays are useful for diagnosis of localized or metastatic cancer. The anti-peptide antibodies were also demonstrated to be useful in the diagnosis of human colon carcinoma by immunohistology (Table 2).

Table 2 is a summary of an immunohistology case review of human colon cancer cases demonstrating that antibodies directed against the peptides in Table 1 can be used to identify enzyme antigen associated with malignant tumor cells.

TABLE 2

| TYPE IV COLLAGENASE IMMUNOREACTIVITY ANTI PEPTIDE ANTIBODY | |
|---|---|
| TISSUE | POSITIVE/TOTAL |
| NORMAL GASTRIC MUCOSA | 0/20 |
| GASTRIC CARCINOMA | |
| CONFINED TO MUCOSA | 18/20* |
| INVADING THE SUBMUCOSA | 20/20** |
| INVADING FULL THICKNESS | 20/20** |
| NORMAL COLORECTAL MUCOSA | 0/10 |
| NEOPLASTIC COLONIC POLYPS | 1/10 |
| COLORECTAL CARCINOMA | |
| CONFINED TO MUCOSA | 1/10* |
| INVADING THE SUBMUCOSA | 8/10** |
| INVADING FULL THICKNESS | 18/20** |

*10-30% TUMOR CELL REACTIVITY
**50-80% TUMOR CELL REACTIVITY

EXAMPLE 3

Antibodies Recognizing Metalloproteinase Peptides

Methods

Protein Peptides

Synthesis of the protein peptides was carried out on a Biosearch Model 9600 peptide synthesizer using standard Merrifield solid-phase peptide synthesis protocols. The primary sequence synthesized was VAAHEFG-HAMGLEHSQ which corresponds exactly to residues 371-386 in human type IV collagenase as shown in FIG. 1. The three His and the two Glu residues were replaced in various combinations with Ala residues and the effect of this substitution on the type IV collagenase and zymogram gelatinase activity was investigated.

Preparation of Antipeptide Antibodies

The preparation of antipeptide antibodies utilized the following steps.

Conjugation of the peptide to BSA: To make the peptide antigenic, it must be covalently bound to BSA or another antigenic protein. To 2 mg of peptide is added one ml of PBS, and to 6 mg of BSA is added 4 ml of PBS. These solutions are combined and 5 ml of 0.25% glutaraldehyde solution is then added to this mixture. The resulting solution is stirred at room temperature for 4 hours, then dialyzed against 1 liter of PBS overnight at room temperature. The next day, the solution is concentrated to 6 ml and dispensed in 1 ml aliquots for immunization.

Immunization of rabbits: To ensure as much as possible high titers of antibody, all immunizations should be carried out using complete Freund's adjuvant. For the first two injections, 1 ml of BSA-peptide conjugate and 1 ml of CFA are emulsified and two rabbits are injected s.c. on the back with 1 ml of emulsion at approximately 30 sites. After the second injection, 0.5 ml of conjugate solution is diluted with 0.5 ml of PBS when making the emulsion. Immunizations are done every two weeks; a bleeding is done prior to immunization, and again the weeks between injections, beginning with the third or fourth injection.

Preparation of peptide antibody affinity resin: Once the anti-peptide antibody serum becomes available, the next step is to do an affinity purification step. In the first step, a peptide affinity resin is prepared. Approximately 10-12 ml of Affi-Gel 10 (BioRad Co.) is quickly washed 3X with 40 ml of cold PBS, and resuspended in cold PBS to give a total volume of about 20 ml. At the same time, 2 mg of peptide is dissolved in 1 ml of PBS, and added to the Affi-Gel suspension with immediate mixing. The resulting mixture is gently agitated overnight in the cold. The next day, sufficient 1M Tris HCl, pH 8.0, is added to make a 0.2M solution, and the gel agitated an additional 4 hours in the cold. The gel is ready for antibody adsorption after washing 3X with 40 ml of PBS.

Affinity purification of antibody: The antibody-containing serum is heated at 56° C. for 30 minutes, cooled and mixed with the peptide resin, which was previously allowed to settle and had excess PBS poured off. After gentle agitation overnight in the cold, the gel suspension is poured into a column and washed with two gel volumes of cold 1M acetic acid followed by 1 gel volume of PBS. The antibody eluate is taken to approximately pH 7.0 with 6N NaOH, and the resulting solution is diaflo (YM-30) concentrated to about 5 ml, with buffer exchanged to PBS.

Coupling antibody to resin: The procedure is much the same as above, except that antibody coupling is allowed to go only 1 hour before Tris is added to stop the reaction and cap up unused active sites.

Immunoassays: Enzyme-linked immunosorbent assays, Western blotting studies, and immunohistology was conducted using standardized, well-accepted methods.

Polyclonal or monoclonal antibodies to the peptides chosen and purified as described above can be labeled with suitable radioactive, enzymatic or fluorescent labels by conventional methods, which should be apparent to those skilled in the art. Immunologic assays employing peptides and antibodies described herein can be applied to biologic samples of any type including body fluids, tissue extracts, or tissue sections, using conventional immunologic methods and with the aid of unlabeled, bound, or unbound antibodies or peptides. Antibodies or peptides can be coupled to suitable solid phase supports such as micro-titer wells. The described antipeptide antibodies for type IV collagenase have significant advantages over antibodies made against native whole enzyme (28). Firstly, they recognize specific domains unique to type IV collagenase which are not homologous to other prevalent metalloproteinases. This is non-obvious and overcomes a significant problem in that large proportions of the amino acid sequence of type IV collagenase is highly homologous or even identical with other metalloproteinases as shown in FIG. 2. Antibodies made against the peptides in Table 1 distinguish type IV collagenase from other metalloproteinases and furthermore can distinguish activated from latent enzyme. This latter feature is very important because pathologic situations could exist in which the ratio of latent to activated enzyme is the determining factor in disease diagnosis or prognosis. It is obvious to those skilled in the art that modifications in the flanking sequences of the peptide inhibitors described herein may alter stability, activity, or specificity toward individual members of the metalloproteinase family. For example, the choice of the specific sequences to the left of the activation associated cleavage site indicated in FIG. 10 may cause the inhibitor to preferentially inhibit stromelysin or type I collagenase compared to type IV collagenase. This is because this region of the sequence shows some variability between the different metalloproteinase types. It is further obvious that certain substitutions of amino acid choices in non-critical regions of the peptides may not significantly alter the inhibitory properties of the peptide. Finally, it is known in the art that recombinant protein peptides can have activity comparable to natural peptides or synthetic peptides. The embodiments of the invention can therefore obviously be produced using suitable cDNA clones inserted into appropriate expression vectors.

Metalloproteinase inhibitors can be used in the treatment of inappropriate angiogenesis, arthritis, tumor growth, invasion and metastasis, and granulomatous inflammatory conditions such as sarcoidosis. In these conditions, it is possible to estimate the amount of enzyme produced and the amount of peptide inhibitor required to inhibit greater than 90% of the active enzyme as shown in FIG. 11. Therapeutic does of the inhibitory peptide falls within an acceptable pharmacologic range of 10–250 mg/kg/d, with a more preferred dosage being 25–100 mg/kg/d. The dosage for a given patient will depend on the amount of enzyme produced in the patient, the condition and size of the patient. The inhibitors may be given as infusions or by any means which provides ready transmission into the circulation. Lyophylized powders may be "snorted". Preparations for buccal or sublingual administration may also be given. For respiratory tract involvement, the peptides may be administered by inhalation. Aerosols are particularly useful for this purpose. For conditions of the eye, the peptides may be administered as eye drops.

1. Stricklin, G. P., Jeffery, J. J., Roswit, W. T., and Eisen, A. Z. (1983) *Biochemistry* 22, 61–68

2. Goldberg, G. I. Wilhelm, S. L. Kronberger, A. Bauer, E. A., Grant, G. A., and Eisen, A. Z. (1988) *J. Biol. Chem.* 261,6600–6605

3. Hasty, K. A., Jeffery, J. J., Hibbs, M. S., and Welgus, H. G. (1987) *J. Biol Chem.* 262, 10048–10052

4. Fields, G. B., Van Wart, H. E., and Birkedal-Hansen, H. (1987) *J. Biol. Chem.* 262, 6221–6226

5. Grant, G. A., Eisen, A. Z., Marmer, B. L. Rosweit, W. T., and Goldberg, G. I. (1987) *J. Biol. Chem.* 262, 5886–5889

6. Liotta, L. A., Kleinerman, J., Catanzaro, P., and Rynbrandt, D. (1977) *J. Natl. Cancer Inst.* 58, 1427–1439

7. Salo, T., Liotta, L. A., Keski, J., Turpeenniemi-Hujanen, T., and Tryggvason, K. (1982) *Int. J. Cancer* 30P, 669–673

8. Kalebic, T., Garbisa, S., Glaser, B., and Liotta, L. A. (1983) *Science* 221, 281–283

9. Uitto, V. J., Schwartz, D., and Veis, A., (1980) *Eur. J. Biochem.* 105, 409–417

10. Garbisa, S., Ballin, M., Daga-Giordini, D., Fastelli, G., Naturale, M., Negro, A., Semenzato, G., and Liotta, L. A. (1986) *J. Biol. Chem.* 261, 2369–2375

11. Liotta, L. A., Abe, S., Gehron-Robey, P., and Martin, G. R. (1979) *Proc. Natl. Acad. Sci. U.S.A.* 76, 2268–2272

12. Liotta, L. A., Tryggvasson, K., Garbisa, S., Gehron-Robey, P., and Abe, S., (1981) *Biochemistry* 20, 100–104

13. Salo, T., Liotta, L. A., and Tryggvason, K, (1983) *J. Biol. Chem.* 258, 3058–3063

14. Liotta, L. A., Tryggvason, K., Garbisa, S., Hart, I., Foltz, C. M., and Shafie, S. (1980) *Naturre*(Lond.) 284, 67–68

15. Muschel, R., Williams, J. E., Lowy, D. R., and Liotta, L. A., (1985) *Amer. J. Pathol.* 121, 1–8

16. Garbisa, S., Pozzatti, R., Muschel, R. J., Saffiotti, U., Ballin, M., Goldfarb, R. H., Khoury, G., and Liotta, L. A. (1987) *Cancer Res.* 47, 1523–1528

17. Collier, I. E., Wilhelm, S. M., Eisen, A. Z., Marmer, B. L., Grant, G. A., Seltzer, J. L., Kronberger, A., He., C., Bauer, E. A., and Goldberg, G. I. (1988) *J. Biol. Chem.* 263, 6579–6587

18. Fessler, L. I., Duncan, K. G., Fessler, J. H., Salo, T., and Tryggvason, K. (1984) *J. Biol. Chem.* 259, 9783–9789

19. Hoyhtya, M., Turpeenniemi-Hujanen, T., Stetler-Stevenson, W., Krutzsch, H., Tryggvason, K., and Liotta, L. A., (1988) *FEBS Letters* 233, 109–113

20. Heussen, C., and Dowdlem E. B. (1980) *Anal. Biochem* 102, 196–202

21. Herron, G. S., Banda, M. J., Clark, E. J., Gavrilovic, J., and Werb, Z. (1986) *J. Biol. Chem.* 261, 2814–2818

22. Wilhelm, S. M., Collierm I. E., Kronberger, A., Eisen, A. Z., Marmer, B. L., Grant, G. A., Bauer, E. A., and Golgberg, G. I., (1987) *Proc. Natl. Acad. Sci.* 84, 6725–6729

23. Saua, J., Quinones, S., Otani, Y., Nagase, H., Harris, E. D., Jr., and Kurkinen, M., (1988) *J. Biol. Chem.* 263, 6742–6745

24. Murphy, G., McAlpine, C. G., Poll, C. T., and Reynolds, J. J., (1985) *Biochem. Biophys. Acta* 831, 49–58

25. Whitham, S. E., Murphy, G., Angel, P., Rahmsdorf, H.-J., Smith, B. J., Lyons, A., Harris, T. J. R., Reynolds, J. J., Herrlich, P. and Docherty, A. J. P. (1986) *Biochem. J.* 240, 913–916

26. Murphy, G., Cockett, M. I., Stephens, P. E., Smith, B. J., and Docherty, A. J. P. (1987). *Biochem. J.* 248, 265–268

27. Sanchez-Lopez, R., Nicholson, R., Gensel, M. C., Matrisian, L., and Breathnach, R., (1988) *J. Biol. Chem.* 263, 11892–11899

28. Tryggvason, K. and Liotta, L. A. U.S. Pat. No. 4,677,058

29. Mullins, D. E. and Rohrlich, S. T. (1983) *Biochim. Biophys. Acta.* 695, 177–214

What is claimed is:

1. A purified and synthetic peptide that inhibits gelatinase or collagenase which is selected from the group consisting of the sequences:

| | |
|---|---|
| VAAHEFGHAMGLEHSQ; | VAAHEFGAAMGLEHSQ; |
| VAAHELGHSLGLSHST; | VAAHEIGHSLGLFHSA; |
| VVAHELTHAVTDYTAG; and | AAHEEICTTNEGVM. |

2. A fragment of the purified and synthetic peptides of claim 1 which contain the sequence AAHE or VAHE that inhibits gelatinase or collagenase.

3. A composition of matter which is a peptide of claim 1 or claim 2 in a carrier.

* * * * *